US010688187B2

(12) United States Patent
Gadgil et al.

(10) Patent No.: US 10,688,187 B2
(45) Date of Patent: Jun. 23, 2020

(54) LIQUID PHARMACEUTICAL COMPOSITION OF ADALIMUMAB

(71) Applicant: INTAS PHARMACEUTICALS LTD., Ahmedabad (IN)

(72) Inventors: Himanshu Gadgil, Sanand Ahmedabad (IN); Chandresh Chhatbar, Sanand Ahmedabad (IN); Vijaykant Pandey, Sanand Ahmedabad (IN)

(73) Assignee: INTAS PHARMACEUTICALS LTD., Ahmedabad (IN)

( * ) Notice: Subject to any disclaimer, the term of this patent is extended or adjusted under 35 U.S.C. 154(b) by 162 days.

(21) Appl. No.: 15/301,421

(22) PCT Filed: Feb. 18, 2015

(86) PCT No.: PCT/IN2015/000092
§ 371 (c)(1),
(2) Date: Oct. 3, 2016

(87) PCT Pub. No.: WO2015/151115
PCT Pub. Date: Oct. 8, 2015

(65) Prior Publication Data
US 2017/0106090 A1 Apr. 20, 2017

(30) Foreign Application Priority Data
Apr. 2, 2014 (IN) .......................... 1248/MUM/2014

(51) Int. Cl.
| A61K 39/395 | (2006.01) |
| A61K 47/26 | (2006.01) |
| A61K 9/00 | (2006.01) |
| C07K 16/24 | (2006.01) |
| A61K 9/19 | (2006.01) |
| A61K 9/08 | (2006.01) |

(52) U.S. Cl.
CPC ............ *A61K 47/26* (2013.01); *A61K 9/0019* (2013.01); *A61K 9/08* (2013.01); *A61K 9/19* (2013.01); *A61K 39/39591* (2013.01); *C07K 16/241* (2013.01)

(58) Field of Classification Search
None
See application file for complete search history.

(56) References Cited

U.S. PATENT DOCUMENTS

| 5,580,856 A | 12/1996 | Prestrelski et al. |
| 6,171,586 B1 | 1/2001 | Lam et al. |
| 7,648,702 B2 | 1/2010 | Gombotz et al. |
| 8,206,714 B2 | 6/2012 | Salfeld et al. |
| 8,216,583 B2 | 7/2012 | Kruase et al. |
| 8,420,081 B2 | 4/2013 | Fraunhofer et al. |
| 2012/0263731 A1* | 10/2012 | Fraunhofer ...... A61K 39/39591 424/142.1 |
| 2014/0044708 A1 | 2/2014 | Dauty et al. |
| 2014/0186361 A1* | 7/2014 | Manning ................ A61K 47/12 424/142.1 |

FOREIGN PATENT DOCUMENTS

| EP | 1314437 | 5/2003 |
| EP | 1478394 | 7/2008 |
| EP | 2946765 A1 | 11/2015 |
| WO | 2009073569 A2 | 6/2009 |
| WO | 2013063510 A1 | 5/2013 |
| WO | 2013164837 | 11/2013 |
| WO | 2014039903 A2 | 3/2014 |
| WO | 2016120413 A1 | 8/2016 |

OTHER PUBLICATIONS

International Search Report for PCT/IN2015/000092, Completed by the Indian Patent Office dated Jul. 22, 2015, 4 Pages.
Weinblatt ME et al. Arthritis and Rheumatism Jan. 2003, vol. 48, No. 1, pp. 35-45, "Adalimumab, a fully human anti-tumor necrosis factor alpha monoclonal antibody, for the treatment of rheumatoid arthritis in patients taking concomitant methortrexate: the ARMADA trial".
Kay et al. Core Evidence 2009, vol. 4, pp. 159-170, "Golimumab: A novel human anti-TNF-amonoclonal antibody for the treatment of rheumatoid arthritis, ankylosing spondylitis, and psoriatic arthritis".
Elliott et al. The Lancet Oct. 22, 1994, vol. 344, Issue No. 8930, pp. 1105-1110, "Randomised double-blind comparison of chimeric monoclonal antibody to tumour necrosis factor alpha (cA2) versus placebo in rheumatoid arthritis".
Jespers et al. Biotechnology Sep. 1994, vol. 12, pp. 899-903, "Guiding Selection of Human Antibodies from Phage Display Repertoires to a Single Epitope of an Antigen".
Supplementary European Search Report for EP 15774333, dated Oct. 27, 2017, 4 Pages.
European Search Opinion for EP 15774333, dated Oct. 27, 2017, 4 Pages.

* cited by examiner

Primary Examiner — Yunsoo Kim
(74) Attorney, Agent, or Firm — Brooks Kushman P.C.

(57) ABSTRACT

A liquid pharmaceutical composition having an anti-TNFα antibody, a buffer, a stabilizer, and a surfactant.

3 Claims, 10 Drawing Sheets

Figure 1: CEX trend analysis of Formulation – 1, 2 & 3

Figure 2: SEC trend analysis of Formulation 1, 2 & 3

Figure 3: DSC profile of Formulation 1

Figure 4: DSC profile of Formulation 2

Figure 5: DSC profile of Formulation 3

Figure 6: DSC profile of Reference formulation

Figure 7: CEX trend analysis of Formulation 1, 2 & 3 buffers

Figure 8: CEX trend analysis of Formulation 1, 2 & 3 buffers (RT)

Figure 9: CEX trend analysis of Formulation 1, 2 & 3 buffers (AT)

Figure 10: SEC trend analysis of Formulation 1, 2 & 3 buffers

Figure 11: SEC trend analysis of Formulation 1, 2 & 3 buffers (RT)

Figure 12: SEC trend analysis of Formulation 1, 2 & 3 buffers (AT)

LIQUID PHARMACEUTICAL COMPOSITION OF ADALIMUMAB

CROSS-REFERENCE TO RELATED APPLICATION

This application is the U.S. national phase of PCT Application No. PCT/IN2015/000092 filed on Feb. 18, 2015, which claims priority to IN Patent Application No. 1248/MUM/2014 filed on Apr. 2, 2014, the disclosures of which are incorporated in their entirety by reference herein.

RELATED APPLICATIONS

This application is related to Indian Provisional Application 1248/MUM/2014 filed 2 Apr. 2014 and is incorporated herein in its entirety.

FIELD OF THE INVENTION

The present invention relates to a liquid pharmaceutical composition comprising an anti-TNFα antibody, buffer, sugar, and surfactant.

BACKGROUND OF THE INVENTION

Tumor necrosis factor is a polypeptide cytokine involved in inflammation and the acute phase response. TNF-alpha is present in larger quantities in persons with rheumatoid arthritis or Crohn's disease. It is also involved in Juvenile Idiopathic Arthritis (JIA), Psoriatic Arthritis (PA), Ankylosing Spondylitis (AS), Ulcerative Colitis and Plaque Psoriasis. Direct inhibition of TNF-alpha by the biological agents has produced significant advances in rheumatoid arthritis and other auto-immune disease treatment and has validated the extra-cellular inhibition of this pro-inflammatory cytokine as an effective therapy. One such biological agent is Adalimumab.

Adalimumab (Anti-TNFα antibody), marketed as HUMIRA® by Abort Inc., is a recombinant human IgG1 monoclonal antibody specific for human tumor necrosis factor (TNF). Adalimumab was created using phage display technology resulting in an antibody with human derived heavy and light chain variable regions and human IgG1 constant regions. Adalimumab is produced by recombinant DNA technology in a mammalian cell expression system and is purified by a process that includes specific viral inactivation and removal steps. It consists of 1330 amino acids and has a molecular weight of approximately 148 kilodaltons.

Generally, proteins have a very short half-life, and undergo denaturation (such as aggregation, dissociation, and adsorption on the surface of vessels) upon exposure to various factors such as unfavorable temperatures, water-air interface, high-pressure, physical/mechanical stress, organic solvents and microbial contamination. Consequently, the denatured protein loses intrinsic physicochemical properties and physiological activity. Denaturation of proteins is often irreversible, and therefore proteins, once denatured, may not recover their native properties to the initial state.

In the biopharmaceutical industry, the long term storage of proteins, prepared using recombinant DNA technology in aqueous formulations, is generally a difficult task. To overcome the stability problem of proteins in aqueous formulations, therapeutic protein products are made more stable via lyophilization (freeze-drying). Lyophilized products are usually accompanied by sterile aqueous media for reconstitution. After reconstitution, the formulations typically have short useful storage lives, even when stored at low temperatures (e.g., 5° C.). Example of TNF alpha inhibitors which are available in the market in the lyophilized form are Enbrel® and Remicade® and both the compositions should be reconstituted before use.

Typical practices to improve polypeptide stability can be addressed by varying the concentration of elements with the formulation, or by adding excipients to modify the formulation.

U.S. Pat. No. 5,580,856 discloses the stabilization of dried proteins against loss of biological activity in the formulations by adding a reconstitution stabilizer upon rehydration of the dried protein. A kit for producing a formulation by dissolving the dried composition in a solvent containing the reconstitution stabilizer is also described.

U.S. Pat. No. 6,171,586 discloses a stable aqueous pharmaceutical formulation comprising a therapeutically effective amount of an antibody not subjected to prior lyophilization, a buffer maintaining the pH in the range from about 4.5 to about 6.0, a surfactant and a polyol, along with uses for such a formulation.

EP1314437 relates to an invention of stabilized preparations containing an antibody in a glycine buffer and/or a histidine butter and also provides processes for preparing a protein-containing stabilized preparation, comprising adjusting the pH with a basic amino acid or a basic amino acid derivative or a salt thereof.

EP1478394 discloses about the invention that relates to an aqueous pharmaceutical composition suitable for long-term storage of polypeptides containing an Fc domain of an immunoglobulin, methods of manufacture, methods of administration and kits containing same.

U.S. Pat. No. 8,216,583 disclose formulation of human antibodies for treating TNF-α associated disorder. The antibody claimed in the invention is adalimumab. It discloses a liquid aqueous pharmaceutical formulation is described which has a high protein concentration, a pH of between about 4 and about 8, and enhanced stability.

U.S. Pat. No. 8,420,081 discloses an aqueous formulation comprising water and a protein, and methods of making the same. The invention is directed towards the findings that proteins formulated in water maintain solubility, as well as stability, even at high concentrations, during long-term liquid storage or other processing steps, such as freeze/thawing and lyophilization.

Hence, there is a need for a stable aqueous pharmaceutical formulation with an extended shelf life, comprising an antibody which is suitable for therapeutic use to inhibit or counteract detrimental TNFα activity. There is also a need for a stable aqueous pharmaceutical formulation with an extended shelf life, comprising an antibody suitable for therapeutic use which is easily administered and contains a high protein concentration.

OBJECT OF THE INVENTION

The main object of the present invention is to provide a novel and stable pharmaceutical composition of anti-TNFα antibody along with pharmaceutically acceptable carriers.

Another object of the present invention is to provide a novel and stable pharmaceutical composition comprising adalimumab (anti-TNFα antibody), buffer, stabilizer, surfactant and pH range of 4.5 to 6.5.

Yet another object of the present invention is to provide a novel and stable pharmaceutical composition of anti-TNFα antibody comprising a buffer system selected from the group consisting of glycine, acetate, arginine, succinate, histidine either alone or a combination thereof.

Yet another object of the present invention is to provide a novel and stable pharmaceutical composition of anti-TNFα antibody comprising sugar or polyol stabilizer selected from the group consisting of monosaccharide such as glucose and mannose, and the like either alone or in combination thereof, disaccharides such as sucrose, trehalose, and maltose, and the like either alone or in combination thereof, sugar alcohols; such as mannitol and xylitol, and the like either alone or in combination thereof.

Yet another object of the present invention is to provide a novel and stable pharmaceutical composition of anti-TNFα antibody comprising the ionic surfactant selected from the group consisting of a polysorbate-based non-ionic surfactant and a poloxamer-based non-ionic surfactant or a combination thereof.

Yet another object of the present invention is to provide a novel and stable pharmaceutical composition of anti-TNFα antibody wherein the formulation is maintained at a pH of about 4.5 to 6.5, more preferably at pH 5.0 to 6.0, in a buffer system selected from the group consisting of glycine, acetate, arginine, succinate, histidine either alone or a combination thereof.

Yet another object of the present invention is to provide a novel and stable pharmaceutical composition which encompasses adalimumab as anti-TNFα antibody comprising glycine, acetate and arginine as buffer either alone or in combination thereof, sucrose as stabilizer, polysorbate 80 as surfactant and formulation is maintained at pH of about 5.0 to 6.0.

Yet another object of the present invention is to provide a novel and stable pharmaceutical composition comprising adalimumab as anti-TNFα antibody, buffer, stabilizer and surfactant; wherein buffer is at concentration of 5 mM to 25 mM and wherein the pH of the composition is in a range of about 4.5 to 6.5; wherein stabilizer is at concentration of 0.1% to 20% w/v; wherein surfactant is at concentration of 0.004% to 0.4% w/v.

SUMMARY OF THE INVENTION

The main aspect of the present invention is to provide a novel and stable pharmaceutical composition of anti-TNFα antibody along with pharmaceutically acceptable carriers.

Another aspect of the present invention is to provide a novel and stable pharmaceutical composition comprising adalimumab (of anti-TNFα antibody), buffer, stabilizer, surfactant and pH range of 4.5 to 6.5.

Yet another aspect of the present invention is to provide a novel and stable pharmaceutical composition of anti-TNFα antibody comprising a buffer system selected from the group consisting of glycine, acetate, arginine, succinate, histidine either alone or a combination thereof.

Yet another aspect of the present invention is to provide a novel and stable pharmaceutical composition of anti-TNFα antibody comprising sugar or polyol stabilizer selected from the group consisting of monosaccharide such as glucose and mannose, and the like either alone or in combination thereof, disaccharides such as sucrose, trehalose, and maltose, and the like either alone or in combination thereof, sugar alcohols such as mannitol and xylitol, and the like either alone or in combination thereof.

Yet another aspect of the present invention is to provide a novel and stable pharmaceutical composition of anti-TNFα antibody comprising the ionic surfactant selected from the group consisting of a polysorbate-based non-ionic surfactant and a poloxamer-based non-ionic surfactant or a combination thereof.

Yet another aspect of the present invention is to provide a novel and stable pharmaceutical composition of anti-TNFα antibody wherein the formulation is maintained at a pH of about 4.5 to 6.5, more preferably at pH 5.0 to 6.0, in a buffer system selected from the group consisting of glycine, acetate, arginine, succinate, histidine, arginine either alone or a combination thereof.

Yet another aspect of the present invention is to provide a novel and stable pharmaceutical composition which encompasses adalimumab as anti-TNFα antibody comprising glycine, acetate and arginine as buffer either alone or in combination thereof, sucrose as stabilizer, polysorbate 80 as surfactant and formulation is maintained at pH of about 5.0 to 6.0.

Yet another aspect of the present invention is to provide a novel and stable pharmaceutical composition comprising adalimumab as anti-TNFα antibody, buffer, stabilizer and surfactant; wherein buffer is at concentration of 5 mM to 25 mM and wherein the pH of the composition is in a range of about 4.5 to 6.5; wherein stabilizer is at concentration of 0.1% to 20% w/v; wherein surfactant is at concentration of 0.004% to 0.4% w/v.

DETAILED DESCRIPTION OF THE INVENTION

The following definitions are provided to facilitate understanding of certain terms used throughout the specification.

The present invention relates to a liquid pharmaceutical composition comprising an anti-TNFα antibody, buffer, sugar, and surfactant.

The term "human TNFα" (which may be abbreviated as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. Treatment with anti-TNF monoclonal antibodies (infliximab, adalimumab and certolizumab pegol) has been shown to provide substantial benefit to patients through reductions in both localized and systemic expression of markers associated with inflammation.

The present invention relates to a novel and stable pharmaceutical composition comprising adalimumab (of anti-TNFα antibody), buffer, stabilizer and surfactant having pH range of 4.5 to 6.5.

Adalimumab is the first phage-display-derived human antibody brought into the clinic, and was generated by 'guided selection' using a mouse monoclonal antibody. (Jespers L. S., Biotechnology 12, 899-903, 1994). Adalimumab (Anti-TNFα antibody), marketed as HUMIRA® by Abott Inc., is a recombinant human IgG1 monoclonal antibody specific for human tumor necrosis factor (TNF). Adalimumab was created using phage display technology resulting in an antibody with human derived heavy and light chain variable regions and human IgG1 constant regions. Adalimumab is produced by recombinant DNA technology in a mammalian cell expression system and is purified by a process that includes specific viral inactivation and removal steps. It consists of 1330 amino acids and has a molecular weight of approximately 148 kilodaltons.

In the present invention, buffers are required for maintaining pH of the formulation. The buffer system of the present invention comprises glycine, acetate, arginine, succinate, histidine either alone or a combination thereof giving desired pH range from 4.5 to 6.5.

In one embodiment, stabilizers used in the present invention are selected from the group that consists of: sugar or polyol stabilizer selected from the group consisting of monosaccharide such as glucose and mannose, and the like either alone or in combination thereof, disaccharides such as sucrose, trehalose, and maltose, and the like either alone or in combination thereof, sugar alcohols such as mannitol and xylitol, and the like either alone or in combination thereof.

In the present invention, surfactant is used in order to prevent adsorption of antibody on the surface of the vial, ampoule, carpoule, cartridge or syringe. Surfactants lower surface tension of a protein solution, thereby, preventing its adsorption or aggregation on to a hydrophobic surface. Preferred surfactants of the present invention include a polysorbate based non-ionic surfactant and polyoxyethylene copolymer, polyvinylpyrrolidone, either alone or in combination.

The novel aqueous pharmaceutical composition of anti-TNFα antibody described in the present invention has the following advantages:
1. Involves use of a buffer system which is selected from the group consisting of glycine, acetate, arginine either alone or a combination thereof maintains the pH of the formulation between 4.5 to 6.5, more preferably between 5.0 to 6.0 and also maintains the purity of the formulation at elevated temperature.
2. Involves use of surfactant to prevent adsorption of anti-TNFα antibody on container.
3. Involves use of a stabilizer which provides better stability.
4. The pharmaceutical composition of present invention is maintained at pH between 5.0 to 6.0 which is critical in maintaining the purity and stability of the aqueous composition at elevated temperatures during storage.
5. Involves operational simplicity.

The specific embodiments described herein are offered by way of example only, and the invention is to be limited by the terms of the appended claims, along with the full scope of equivalents to which such claims are entitled.

Example 1

Screening and Selection of Buffer

TABLE 1

Formulation composition

| Components | Ingredient | Formulation 1 | Formulation 2 | Formulation 3 | Reference formulation (Generic DP) |
|---|---|---|---|---|---|
| Active Protein | Adalimumab DS | 50 mg/mL | 50 mg/mL | 50 mg/mL | 50 mg/mL |
| Buffer | Glycine | 15 mM | — | — | — |
|  | Acetate | — | 10 mM | — | — |
|  | Arginine | — | — | 15 mM | — |
|  | Phosphate | — | — | — | 14.1 mM |
|  | Citrate | — | — | — | 7.21 mM |
| Stabilizer and Isotonicity modifier | Sucrose | 9.5% | 9.5% | 9.5% | — |
|  | Mannitol | — | — | — | 1.2% |
|  | Sodium Chloride | — | — | — | 0.62% |
| Nonionic surfactant | Polysorbate 80 | 0.1% | 0.1% | 0.1% | 0.1% |
| Vehicle | Water for injection | Qs to 1 mL | Qs to 1 mL | Qs to 1 mL | Qs to 1 mL |

Method of Preparation:

Adalimumab formulation was prepared in formulation composition given in the above table by dissolving the excipients in water for injection. The protein concentration was set to 50 mg/mL and the pH of the formulation is set to 5.2 similar to the reference formulation. 0.8 mL solution filled in 2 mL USP type 1 vial and sealed with coated bromobutylated rubber stopper and aluminum seal. Filled vial were charged at 40° C. for 15 days stress stability study. During stability study following test were done:

TABLE 2

Purpose of the tests

| Tests | Purpose of the tests |
|---|---|
| SEC-HPLC | To monitor aggregates (H.M.W. impurities) |
| CEX HPLC | To monitor charge related impurities |
| DSC | To monitor effect on thermo stability profile |

TABLE 2-continued

| Tests | Purpose of the tests |
|---|---|
| Potency | To monitor effect on in vitro bioassay |
| pH | To monitor effect on pH |
| Physical appearance | To monitor physical appearance |

Stress Stability Data (14 Day at 40° C.) for Selection of Buffer:

a) Physical Appearance:

All the samples were observed to be clear and colorless till 14 Day at 40° C. for ST.

b) pH:

TABLE 3 pH of Formulation 1, 2 & 3

| Buffers | pH Time point | |
|---|---|---|
| | 0 D | 14 D |
| Formulation 1 | 5.4 | 5.2 |
| Formulation 2 | 5.3 | 5.2 |
| Formulation 3 | 5.3 | 5.2 |
| Generic DP | 5.2 | 5.2 | c) CEX-HPLC:

Ion exchange chromatography separates analytes based on differences in the surface charge of the molecules and their concomitant varying strengths of interaction with the stationary phase. Charge-related variants expected in Molecule and their variability during storage. Propac WCX-10 column from Thermo Scientific was used on Agilent HPLC.

TABLE 4

Figure 1:
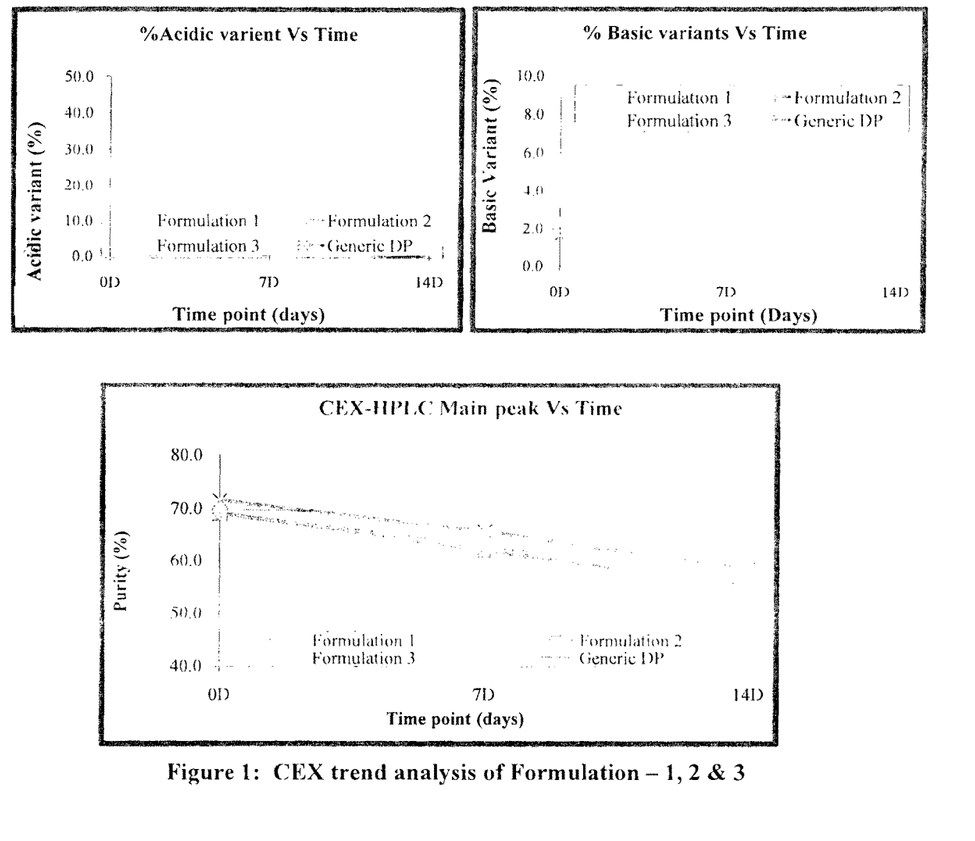
FIG. 1 shows the comparative CEX-HPLC profile of Adalimumab Formulations 1, 2, 3 & RMP at 0D, 7D & 14D days.

CEX data of Formulation 1, 2 & 3 (FIG.-1)

| Buffers | % Purity | | | % Acidic | | | % Basic | | |
|---|---|---|---|---|---|---|---|---|---|
| | 0 D | 7 D | 14 D | 0 D | 7 D | 14 D | 0 D | 7 D | 14 D |
| Formulation 1 | 69.0 | 62.6 | 56.1 | 25.5 | 31.9 | 38.3 | 5.5 | 5.5 | 5.6 |
| Formulation 2 | 69.0 | 61.9 | 55.1 | 25.5 | 32.8 | 39.6 | 5.4 | 5.4 | 5.3 |
| Formulation 3 | 70.6 | 64.3 | 59.1 | 24.2 | 30.3 | 34.5 | 5.2 | 5.4 | 6.4 |
| Generic DP | 71.5 | 65.6 | 58.3 | 26.9 | 31.3 | 37.4 | 1.6 | 3.1 | 4.2 |

Observation: Based on 14 days stress data the purity of the formulation 1, 2 and 3 was comparable with the reference formulation (generic DP). Results are shown in FIG. 1.

d) SEC-HPLC:

Size exclusion chromatography (SEC) is size based separation of molecules. High molecular weight and low molecular weight related variants (HMWs and LMWs) can be resolved and detected using this technique. TSK G3000SWXL (7.8 mm×300 mm) column from Tosoh Haas was used on Agilent HPLC.

TABLE 5

Figure 2:
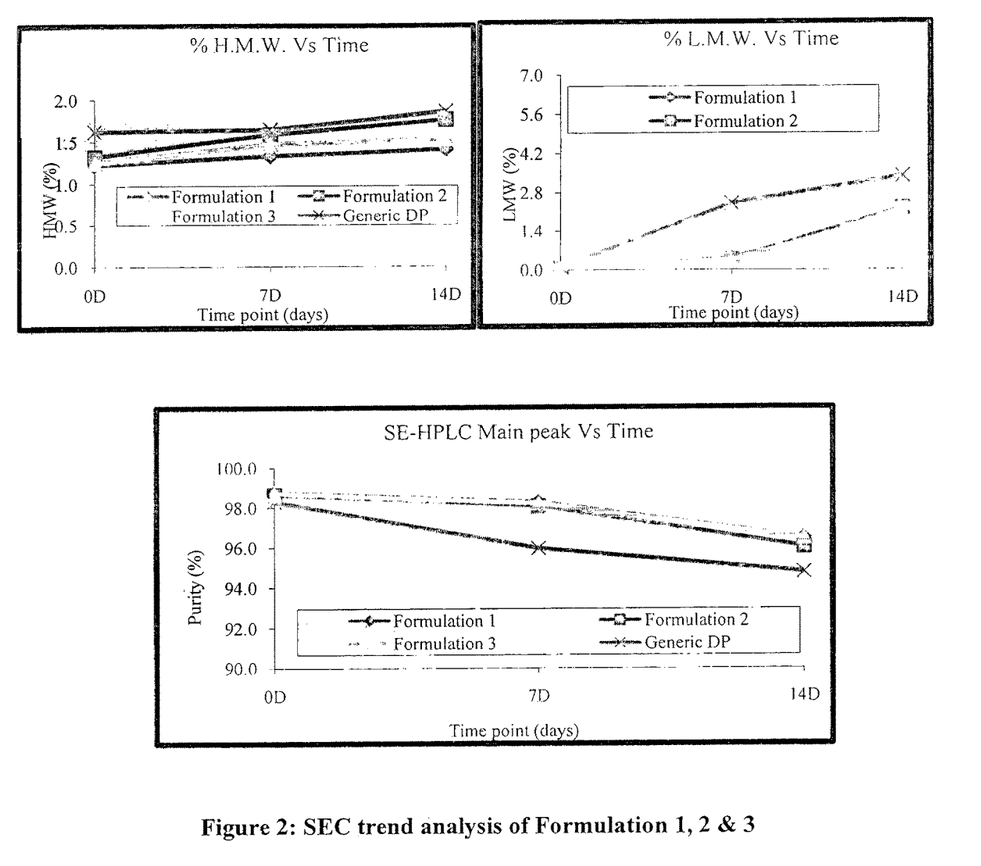
FIG. 2 shows the comparative SEC-H-PLC profile of Adalimumab Formulations 1, 2, 3 & RMP at 0D, 7D & 14D days.
Figure 3:
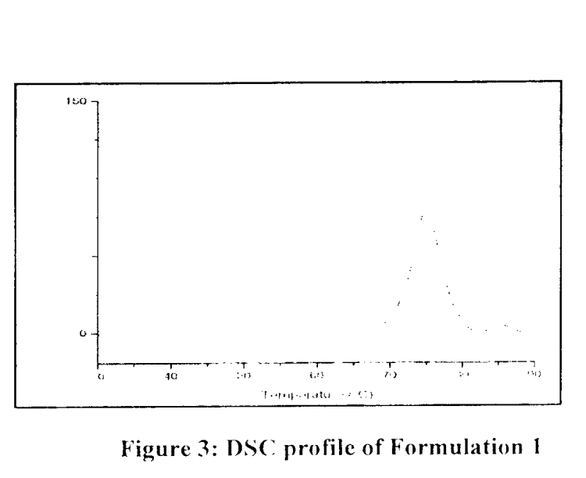
FIG. 3, FIG. 4, FIG. 5 & FIG. 6 shows DSC profile of Formulations 1, 2, 3 & RMP respectively.
Figure 4:
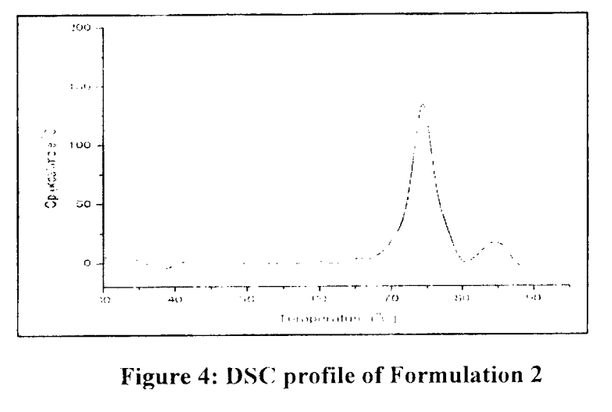
Figure 5:
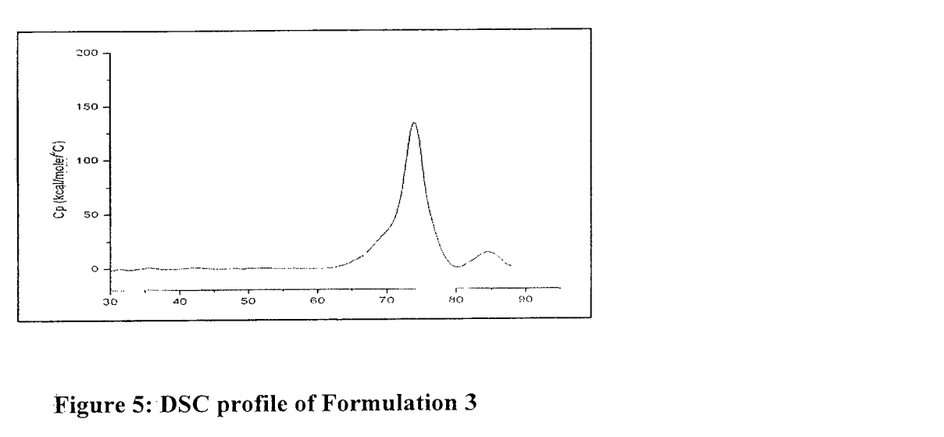
Figure 6:
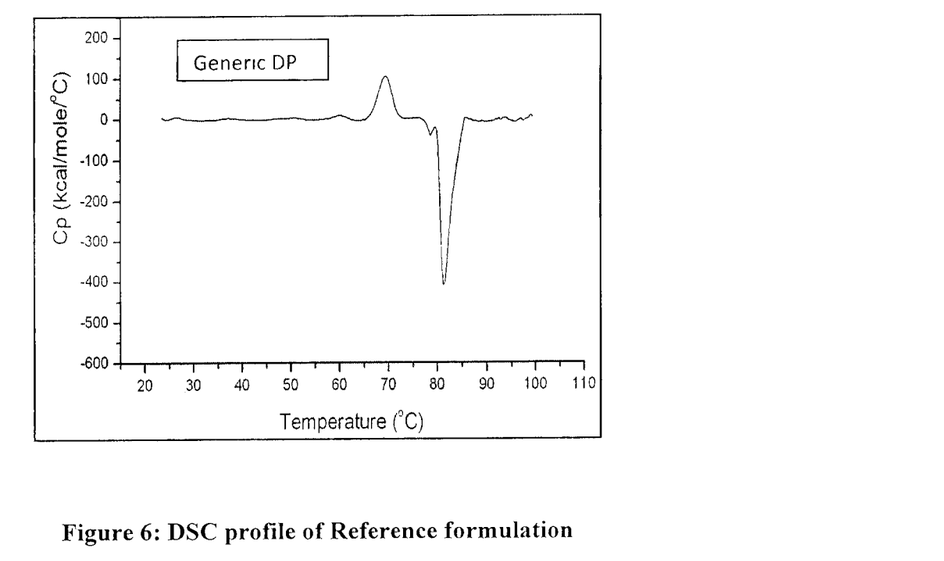

SEC data of Formulation 1, 2 & 3 (FIG.-2)

| Buffers | % Monomer | | | % L.M.W | | | % H.M.W | | |
|---|---|---|---|---|---|---|---|---|---|
| | 0 D | 7 D | 14 D | 0 D | 7 D | 14 D | 0 D | 7 D | 14 D |
| Formulation 1 | 99.5 | 96.1 | 97.6 | 0.0 | 0.4 | 2.1 | 1.2 | 1.3 | 1.4 |
| Formulation 2 | 99.6 | 99.0 | 95.2 | 0.0 | 0.4 | 2.2 | 1.3 | 1.6 | 1.8 |
| Formulation 3 | 99.6 | 97.3 | 97.2 | 0.0 | 0.3 | 2.0 | 1.3 | 1.5 | 1.5 |
| Generic DP | 98.3 | 95.9 | 94.8 | 0.1 | 2.4 | 3.4 | 1.6 | 1.6 | 1.9 |

Observation: Formulation 1, 2 and 3 all shows less HMW and LMW compared to the reference formulation (Generic DP). Results are shown in FIG. 2.

e) Relative Potency:

The biological activity of Adalimumab is determined by cell based in-vitro bio-assay. The assay is based on the neutralization of cytotoxic effect of TNF-α on L929 (mouse connective tissue) cell line expressing TNF receptor 1 (TNFR1). Adalimumab specifically neutralizes the cytotoxic activity of TNF-α in a dose dependent manner.

TABLE 6

% Potency data of Formulation 1, 2 & 3

| Buffers | % Potency Time point | |
|---|---|---|
| | 0 D | 14 D |
| Formulation 1 | 94 | 103 |
| Formulation 2 | 103 | 104 |
| Formulation 3 | 114 | 101 |
| Generic DP | 113 | 110 |

Observation: There is no change in potency at 40° C. after 14 days as compared to initial in all Formulation.

f) Differential Scanning Calorimetry:

DSC measures the difference in heat energy uptake between a sample solution and appropriate reference (buffer/solvent) with increase in temperature. The transition temperatures Tm (where 50% of protein is in folded form, while 50% in unfolded) is indicator of protein stability.

Samples were analyzed on DSC (MicroCal, LLC Microcalorimeter, Model No.: VP-DSC). The scan rate was set to 60 C/h and the protein concentration of the samples loaded was 0.5 mg/mL.

TABLE 7

Tm value of Formulation 1, 2 & 3

| | Batch no. | |
|---|---|---|
| | Tm1 | Tm2 |
| Formulation 1 | 75.0 | 85.4 |
| Formulation 2 | 74.3 | 84.8 |
| Formulation 3 | 74.0 | 84.5 |
| Generic DP | 69.5 | 77.8 |

Observation: The thermo gram of generic DP shows the down fall signal which is exothermic in nature and denote the aggregation of the protein at that temperature. Hence it can be said that the protein in the generic formulation matrix is susceptible to the aggregation. Formulation 1, 2 and 3 shows good thermal stability as compared to the generic formulation and Tm1 and Tm2 shows the higher value for all three formulation as compared to generic formulation. Based on the DSC results it can be predict that the protein (Adalimumab) will be more stable at long term in test formulation 1, 2 and 3 as compared to generic formulation. This can also be seen when correlated with the stress stability data. Results are shown in FIGS. 3 to 6.

Example 2

Stability Test of Adalimumab Aqueous Thermostable Formulation

Rationale:

Based on the above data, all three buffer shows a good buffering capacity, and thermo stability profile. To confirm the results obtained during the initial screening, another set of stability study were carried out with the formulation 1, 2 and 3. Composition of all formulation buffer as given in below table.

TABLE 8

Study condition and Time points for Formulation 1, 2 & 3

| Sr. No. | Condition | Temperature | Time points |
|---|---|---|---|
| 1 | Stress | 40° C. ± 2° C. | 7 D & 14 D |
| 2 | RT | 5° C. ± 3° C. | 1 M, 2 M, 3 M & 6 M |
| 3 | AT | 25° C. ± 2° C. | 1 M, 2 M, & 3 M |

Method of Preparation:

Adalimumab formulation was prepared in formulation composition given in the above table by dissolving the excipients in water for injection. The protein concentration was set to 50 mg/mL and the pH of the formulation is set to 5.2 similar to the reference formulation. 0.8 mL solution filled in 2 mL USP type 1 vial and sealed with coated bromobutylated rubber stopper and aluminum seal. Filled vial were charged at 40° C. for 15 days stress stability study, At 5° C. for 6 months and at 25° C. for 6 months as described in the above table. During stability study following test were done:

TABLE 9

Purpose of the tests

| Tests | Purpose of the tests |
|---|---|
| SE-HPLC | To monitor aggregates (H.M.W. impurities) |
| CEX HPLC | To monitor charge related impurities |
| Potency | To monitor effect on in vitro bioassay |
| pH | To monitor effect on pH |
| Physical appearance | To monitor physical appearance | a) Physical Appearance:

Samples were observed to be clear and colorless till 14D ST, 6M RT & 3M AT.

b) pH

Stress Data: At 40° C.

TABLE 10 pH data of Formulation 1, 2 & 3

| | pH Time point | |
|---|---|---|
| Buffers | 0 D | 14 D |
| Formulation 1 | 5.2 | 5.3 |
| Formulation 2 | 5.2 | 5.3 |
| Formulation 3 | 5.2 | 5.3 |

Real Time Data (At 5° C.)

TABLE 11 pH data of Formulation 1, 2 & 3

| | pH Time point | | | | |
|---|---|---|---|---|---|
| Buffers | 0 D | 1 M | 2 M | 3 M | 6 M |
| Formulation 1 | 5.2 | 5.5 | 5.2 | 5.2 | 5.4 |
| Formulation 2 | 5.3 | 5.4 | 5.4 | 5.5 | 5.4 |
| Formulation 3 | 5.3 | 5.3 | 5.2 | 5.2 | 5.2 |

Accelerated Temperature Date: At 25° C.

TABLE 12 pH data of Formulation 1, 2 & 3

| | pH Time point | | | |
|---|---|---|---|---|
| Buffers | 0 D | 1 M | 2 M | 3 M |
| Formulation 1 | 5.2 | 5.5 | 5.2 | 5.2 |
| Formulation 2 | 5.3 | 5.4 | 5.4 | 5.5 |
| Formulation 3 | 5.3 | 5.3 | 5.2 | 5.2 | c) CEX Data

Stress Data: At 40° C.

TABLE 13

Figure 7:
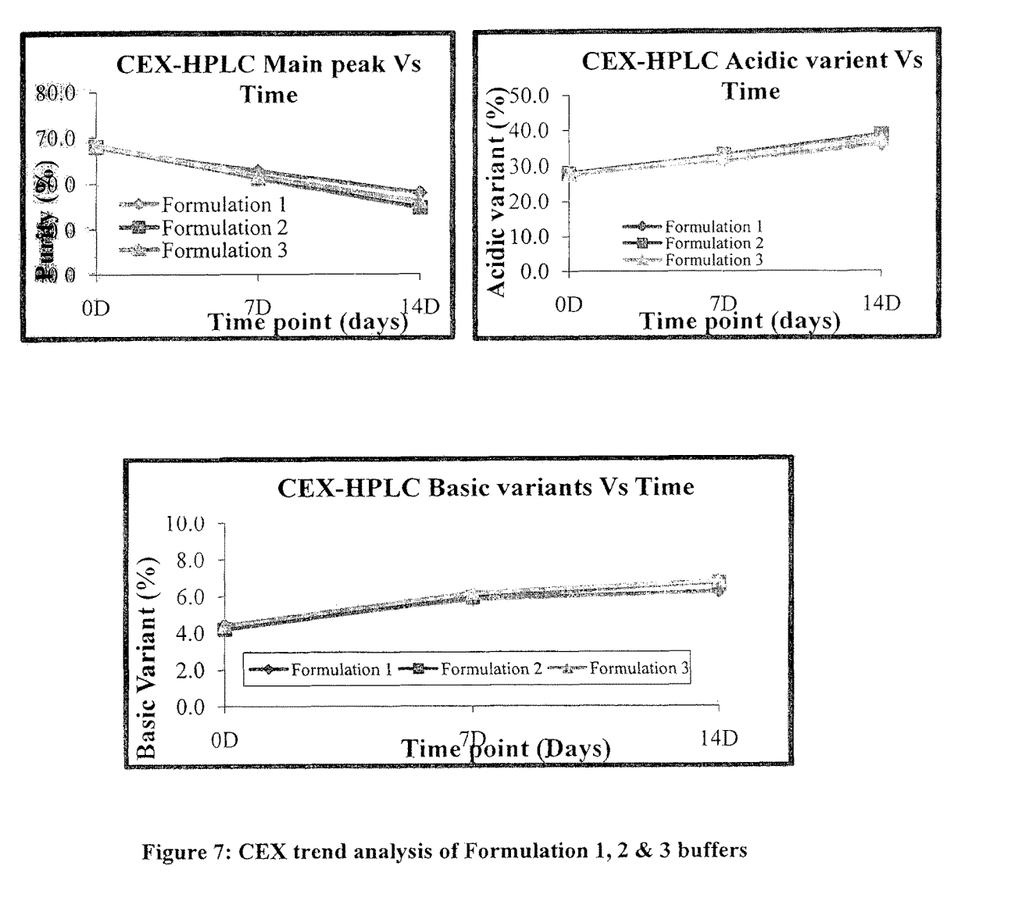
FIG. 7 shows the stress study CEX-HPLC profile of Formulation 1, 2 & 3 at 40° C. for 0D, 7D & 14D days.

CEX data of Formulation 1, 2 & 3 buffers (FIG.-7)

| | % Acidic variants | | | % Principal peak Time points | | | % Basic Variants | | |
|---|---|---|---|---|---|---|---|---|---|
| Buffers | 0 D | 7 D | 14 D | 0 D | 7 D | 14 D | 0 D | 7 D | 14 D |
| Formulation 1 | 28.0 | 31.4 | 35.9 | 67.6 | 62.7 | 57.9 | 4.4 | 5.8 | 6.2 |
| Formulation 2 | 27.8 | 33.0 | 38.7 | 68.0 | 61.1 | 54.6 | 4.2 | 5.9 | 6.7 |
| Formulation 3 | 27.4 | 32.3 | 37.3 | 68.3 | 61.6 | 56.0 | 4.4 | 6.2 | 6.8 |

Observation: All the formulation are showing good stability and comparable. Results are shown in FIG. 7.

Real Time Data (At 5° C.)

TABLE 14

Figure 8:
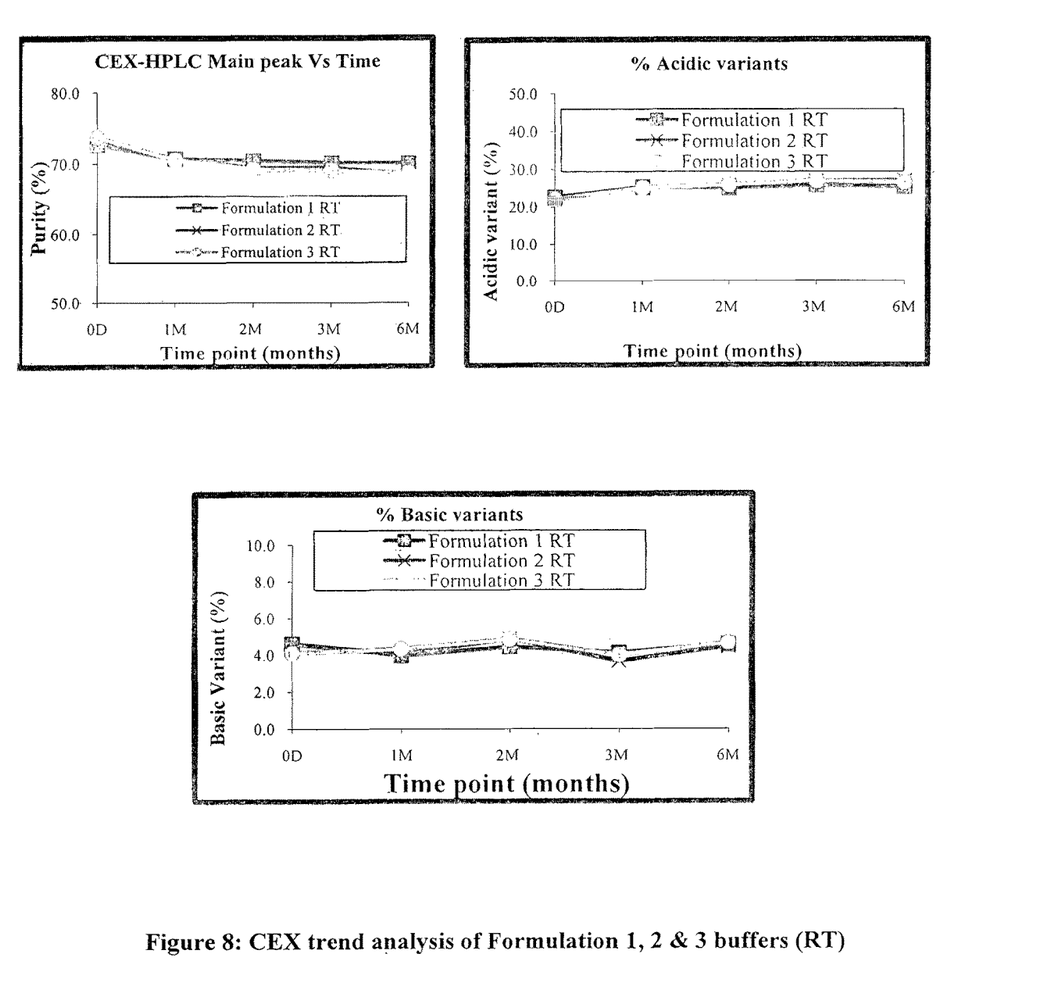
FIG. 8 shows the Real Time (RT) CEX-HPLC profile of Formulation 1, 2 & 3 at 5° C. for 0 day, 1M, 2M, 3M & 6M.

CEX data of Formulation 1, 2 & 3 buffers (RT) (FIG.-8)

| Buffers | % Acidic variants | | | | | % Principal peak | | | | | % Basic Variants | | | | |
|---|---|---|---|---|---|---|---|---|---|---|---|---|---|---|---|
| | 0 D | 1 M | 2 M | 3 M | 6 M | 0 D | 1 M | 2 M | 3 M | 6 M | 0 D | 1 M | 2 M | 3 M | 6 M |
| Formulation 1 | 22.7 | 25.3 | 25.1 | 25.8 | 25.4 | 72.7 | 70.7 | 70.4 | 70.1 | 70.0 | 4.6 | 4.0 | 4.4 | 4.1 | 4.6 |
| Formulation 2 | 22.2 | 25.3 | 25.7 | 26.9 | 27.0 | 73.2 | 70.7 | 69.4 | 69.4 | 68.5 | 4.6 | 4.1 | 4.9 | 3.7 | 4.4 |
| Formulation 3 | 22.1 | 25.1 | 26.0 | 27.0 | 26.7 | 73.8 | 70.5 | 69.1 | 69.0 | 68.6 | 4.1 | 4.3 | 4.9 | 4.0 | 4.7 |

Observation: At 5° C. after 6 month all three formulations shows similar stability profile when analyze by CEX HPLC; there is no significant increase in the acidic or basic variant observed in all three formulation. Results are shown in FIG. 8.

Accelerated Temperature Data: At 25° C.

TABLE 15

Figure 9:
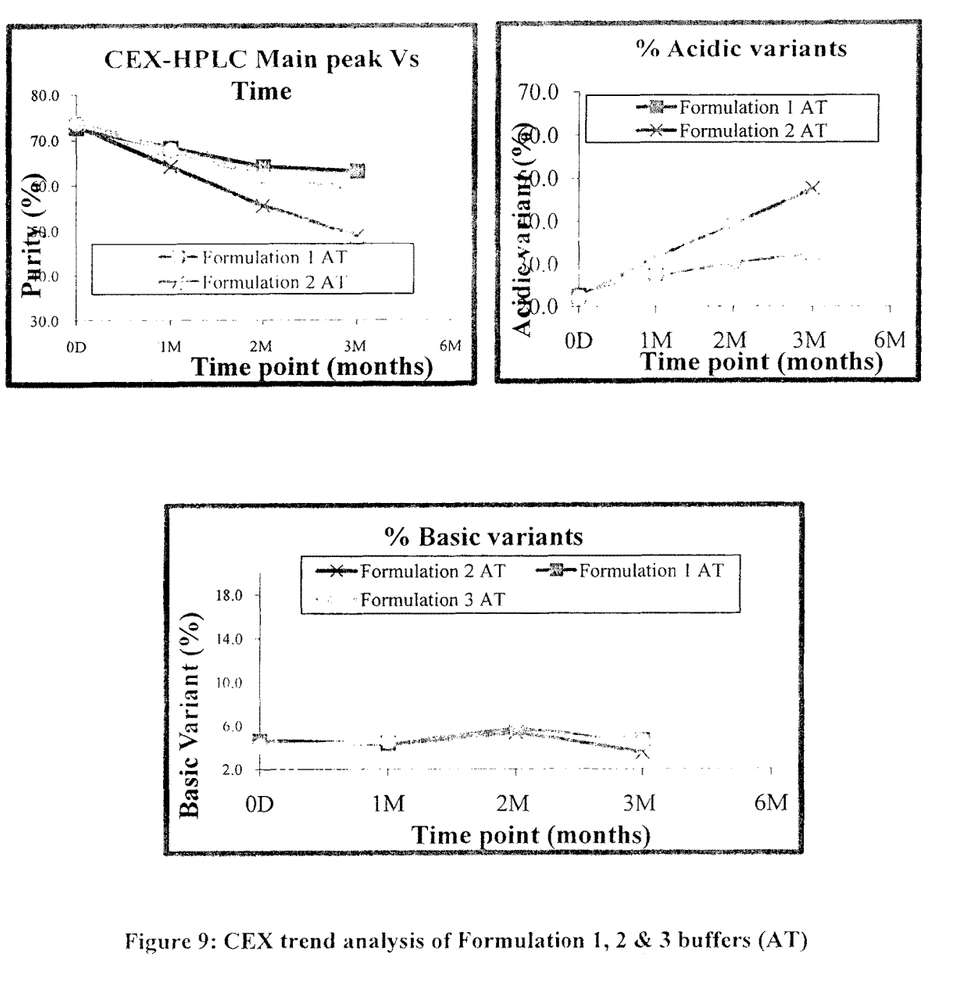
FIG. 9 shows the Accelerated Temperature (AT) CEX-HPLC profile of Formulation 1, 2 & 3 at 5° C. for 0 day, 1M, 2M & 3M.

CEX data of Formulation 1, 2 & 3 buffers (AT) (FIG.-9)

| Buffers | % Acidic variants | | | | % Principal peak | | | | % Basic Variants | | | |
|---|---|---|---|---|---|---|---|---|---|---|---|---|
| | 0 D | 1 M | 2 M | 3 M | 0 D | 1 M | 2 M | 3 M | 0 D | 1 M | 2 M | 3 M |
| Formulation 1 | 22.7 | 27.4 | 30.2 | 32.2 | 72.7 | 68.2 | 64.1 | 63.1 | 4.6 | 4.4 | 5.7 | 4.7 |
| Formulation 2 | 22.2 | 31.6 | 39.2 | 47.7 | 73.2 | 64.2 | 55.5 | 48.8 | 4.6 | 4.3 | 5.3 | 3.5 |
| Formulation 3 | 22.1 | 27.6 | 31.5 | 36.3 | 73.8 | 67.8 | 62.0 | 59.3 | 4.1 | 4.6 | 6.5 | 4.4 |

Observation: The overall stability of all three formulations is good at 25° C. after 3 month. Results are shown in FIG. 9.

d) SEC-HPLC Data

Stress Data: At 40° C.

TABLE 16

Figure 10:
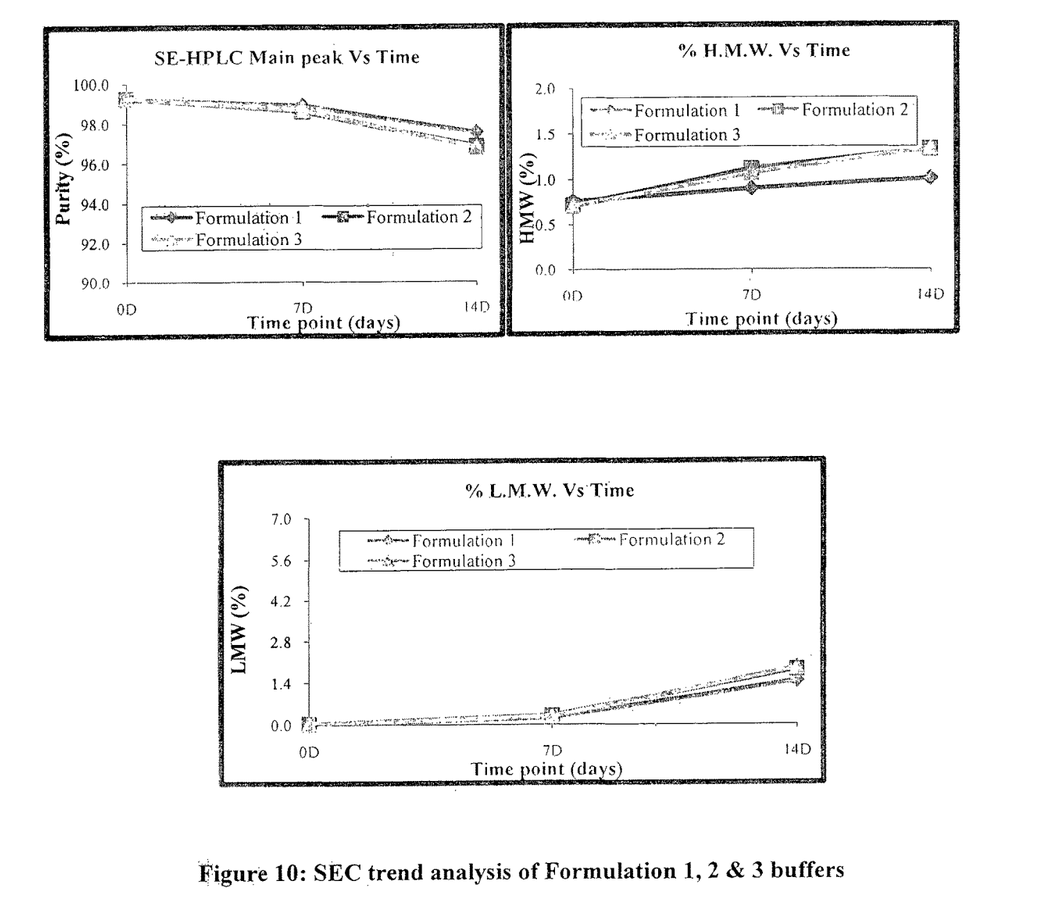
FIG. 10 shows the stress study SEC-HPLC profile of Formulation 1, 2 & 3 at 40° C. for 0D, 7D & 14D days.

SEC data of Formulation 1, 2 & 3 buffers (FIG.-10)

| Buffers | % Monomer | | | % L.M.W | | | % H.M.W | | |
|---|---|---|---|---|---|---|---|---|---|
| | 0 D | 7 D | 14 D | 0 D | 7 D | 14 D | 0 D | 7 D | 14 D |
| Formulation 1 | 99.2 | 98.9 | 97.5 | 0.0 | 0.2 | 1.5 | 0.8 | 0.9 | 1.0 |
| Formulation 2 | 99.3 | 98.6 | 96.8 | 0.0 | 0.3 | 1.8 | 0.7 | 1.1 | 1.3 |
| Formulation 3 | 99.3 | 98.7 | 96.8 | 0.0 | 0.3 | 1.9 | 0.7 | 1.1 | 1.3 |

TABLE 17

% Change in % Purity of Principal peak (SEC) at 14 D ST from initial

| Batch no. | % Change |
|---|---|
| Formulation 1 | 1.7 |
| Formulation 2 | 2.4 |
| Formulation 3 | 2.5 |

Observation: All three formulations are showing good stability and comparable in SEC profile. Results are shown in FIG. 10.

Real Time Data (at 5° C.)

TABLE 18

Figure 11:
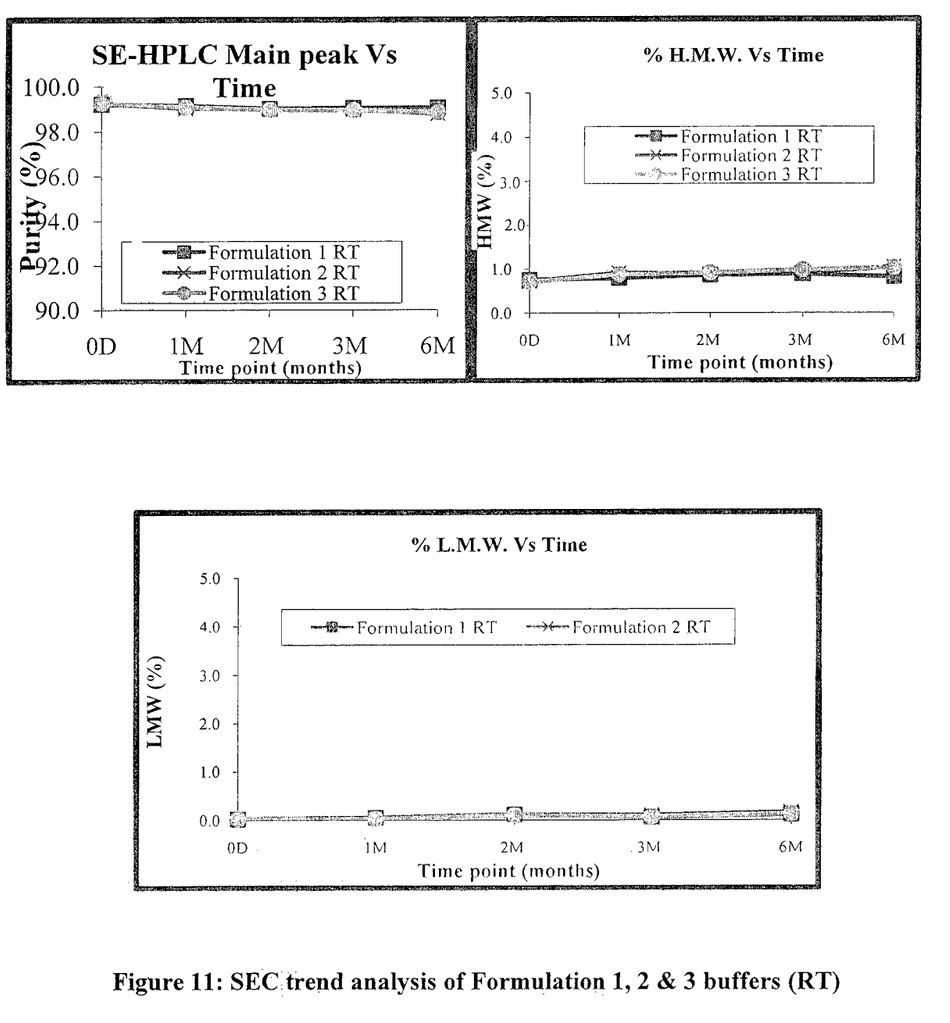
FIG. 11 shows the Real Time (RT) SEC-HPLC profile of Formulation 1, 2 & 3 at 5° C. for 0 day, 1M, 2M, 3M & 6M.

SEC data of Formulation 1, 2 & 3 buffers (RT) (FIG.-11)

| Buffers | % Monomer | | | | | % L.M.W | | | | | % H.M.W | | | | |
|---|---|---|---|---|---|---|---|---|---|---|---|---|---|---|---|
| | 0 D | 1 M | 2 M | 3 M | 6 M | 0 D | 1 M | 2 M | 3 M | 6 M | 0 D | 1 M | 2 M | 3 M | 6 M |
| Formulation 1 | 99.2 | 99.2 | 99.0 | 99.1 | 99.1 | 0.0 | 0.1 | 0.1 | 0.1 | 0.1 | 0.8 | 0.8 | 0.9 | 0.9 | 0.8 |
| Formulation 2 | 99.3 | 99.0 | 99.0 | 99.0 | 98.8 | 0.0 | 0.0 | 0.1 | 0.1 | 0.2 | 0.7 | 0.9 | 0.9 | 0.9 | 1.0 |
| Formulation 3 | 99.3 | 99.1 | 99.0 | 98.9 | 98.8 | 0.0 | 0.0 | 0.1 | 0.1 | 0.1 | 0.7 | 0.9 | 0.9 | 1.0 | 1.0 |

Observation: At 5° C. after 6 month all three formulations shows similar stability profile when analyze by SE HPLC; there is no significant increase in the HMW and LMW observed in all three formulation. Results are shown in FIG. 11.

Accelerated Temperature Data: At 25° C.

TABLE 19

Figure 12:
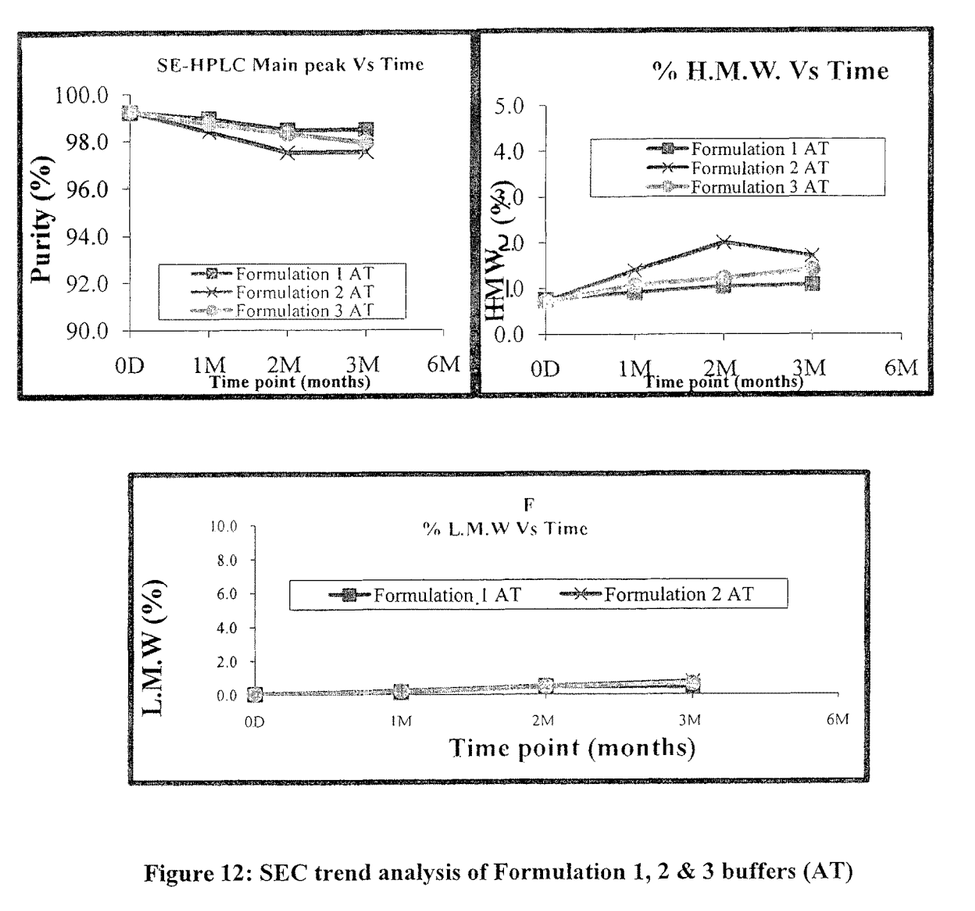
FIG. 12 shows the Accelerated Temperature (AT) SEC-HPLC profile of Formulation 1, 2 & 3 at 5° C. for 0 day, 1M, 2M & 3M.

SEC data of Formulation 1, 2 & 3 buffers (AT) (FIG.-12)

| Buffers | % Monomer | | | | % L.M.W Time points | | | | % H.M.W | | | |
|---|---|---|---|---|---|---|---|---|---|---|---|---|
| | 0 D | 1 M | 2 M | 3 M | 0 D | 1 M | 2 M | 3 M | 0 D | 1 M | 2 M | 3 M |
| Formulation 1 | 99.2 | 99.0 | 98.5 | 98.5 | 0.0 | 0.1 | 0.5 | 0.4 | 0.8 | 0.9 | 1.0 | 1.1 |
| Formulation 2 | 99.3 | 98.4 | 97.5 | 97.5 | 0.0 | 0.2 | 0.5 | 0.8 | 0.7 | 1.4 | 2.0 | 1.7 |
| Formulation 3 | 99.3 | 98.7 | 98.3 | 97.9 | 0.0 | 0.2 | 0.5 | 0.7 | 0.7 | 1.1 | 1.2 | 1.4 |

Observation: At 25° C. after 3 month all three formulations shows similar stability profile when analyze by SE HPLC; there is no significant increase in the HMW and LMW observed in all three formulation. It shows that these formulations are preventing Adalimumab from aggregation and fragmentation. Results are shown in FIG. 12.

e) Potency

Stress Data: At 40° C.

TABLE 20

% Potency data of Formulation 1, 2 & 3 buffers

| Buffers | % Potency Time point | |
|---|---|---|
| | 0 D | 14 D |
| Formulation 1 | 99 | 97 |
| Formulation 2 | 95 | 100 |
| Formulation 3 | 118 | 100 |

Observation: There is no change in potency at 40° C. after 14 days as compared to initial in all formulations.

Real Time Data (At 5° C.)

TABLE 21

% Potency data of Formulation 1, 2 & 3 buffers

| Buffers | % Potency Time point | | | |
|---|---|---|---|---|
| | 0 D | 1 M | 2 M | 3 M |
| Formulation 1 | 99 | 99 | 104 | 120 |
| Formulation 2 | 95 | 107 | 103 | 117 |
| Formulation 3 | 118 | 111 | 114 | 109 |

Observation: There is no change in potency at after 3 Months as compared to initial in all formulations.

Accelerated Temperature Data: At 25° C.

TABLE 22

% Potency data of Formulation 1, 2 & 3 buffers

| Buffers | % Potency Time point | | | |
|---|---|---|---|---|
| | 0 D | 1 M | 2 M | 3 M |
| Formulation 1 | 99 | 110 | 105 | 106 |
| Formulation 2 | 95 | 108 | 92 | 118 |
| Formulation 3 | 118 | 116 | 107 | 99 |

Observation: There is no change in potency at after 3 Months at 25° C. as compared to initial in all formulations.

We claim:

1. An aqueous pharmaceutical formulation of Adalimumab comprising:
   a) 50 mg/mL Adalimumab,
   b) 15 mM glycine buffer,
   c) 9.5% sucrose, and
   d) 0.1% Polysorbate 80 at pH 5.2.

2. An aqueous pharmaceutical formulation of Adalimumab consisting of a glycine buffer, sucrose and Polysorbate 80 at pH 5.2;
   wherein Adalimumab is present at a concentration of 1 mg/mL to 100 mg/mL.

3. The aqueous pharmaceutical formulation as claimed in claim 2 consisting of:
   a) 50 mg/mL Adalimumab,
   b) 15 mM glycine buffer,
   c) 9.5% sucrose, and
   d) 0.1% Polysorbate 80 at pH 5.2.

* * * * *